(12) United States Patent
Asehnoune

(10) Patent No.: US 8,636,979 B2
(45) Date of Patent: Jan. 28, 2014

(54) TLR 4 AND 9 RECEPTORS AGONISTS FOR PREVENTING SEPTIC COMPLICATIONS OF POST-TRAUMATIC IMMUNODEPRESSION IN PATIENTS HOSPITALIZED FOR SEVERE TRAUMATIC INJURIES

(75) Inventor: Karim Asehnoune, Nantes (FR)

(73) Assignees: Chu Nantes, Nantes (FR); Universite de Nantes, Nantes (FR)

( * ) Notice: Subject to any disclaimer, the term of this patent is extended or adjusted under 35 U.S.C. 154(b) by 0 days.

(21) Appl. No.: 13/519,531

(22) PCT Filed: Dec. 17, 2010

(86) PCT No.: PCT/EP2010/070111
§ 371 (c)(1),
(2), (4) Date: Oct. 5, 2012

(87) PCT Pub. No.: WO2011/080126
PCT Pub. Date: Jul. 7, 2011

(65) Prior Publication Data
US 2013/0028936 A1    Jan. 31, 2013

(30) Foreign Application Priority Data

Dec. 28, 2009    (FR) .................................... 09 06372

(51) Int. Cl.
| A61K 49/00 | (2006.01) |
| A61K 39/02 | (2006.01) |
| A61K 45/00 | (2006.01) |

(52) U.S. Cl.
USPC ....... 424/9.1; 424/9.2; 424/184.1; 424/234.1; 424/278.1

(58) Field of Classification Search
USPC .................. 424/9.1, 9.2, 184.1, 234.1, 278.1
See application file for complete search history.

(56) References Cited

U.S. PATENT DOCUMENTS

2006/0265767 A1    11/2006 Beutler et al.

FOREIGN PATENT DOCUMENTS

WO    WO 2005/035588    4/2005

OTHER PUBLICATIONS

Diwan, M., et al. Journal of Drug Targeting, vol. 11, No. 8-11, pp. 495-507.*
Foldes, G. et al, Expert Opinions in Investigative Drugs, vol. 15, No. 8, pp. 857-871, 2006.*
Mutwiri, G., et al. Veterinary Immunology and Immunopathology, vol. 91, pp. 89-103, 2003.*
Luyer, M.D. et al. Annals of Surgery, vol. 245, No. 5, pp. 795-802.*
Thobe, B.M., et al. Journal of Cellular Physiology, vol. 210, No. 3, pp. 667-675, 2007.*

Asehnoune, K., et al., "Modulation différentielle des effets de la stimulation des récepteurs Toll-like 2 et 4 par l'état de choc hémorragique Differential modulation of TLR2 and TLR4-induced TNF production by murin haemorrhagic shock," http://france.elsevier.com/direct/ANNFAR/.
Asehnoune, K., et al., "$\beta_2$-Adrenoceptor blockade partially restores ex vivo TNF production following hemorrhagic shock." Cytokine, 2006, pp. 212-218, vol. 34.
Asehnoune, K., et al., "Influence of resuscitation volume on blood cells TNF production in a murine model of haemorrhage," Resuscitation, 2006, pp. 127-133, vol. 68.
Askew, D., et al., "CpG DNA Induces Maturation of Dendritic Cells with Distinct Effects on Nascent and Recycling MHC-II Antigen-Processing Mechanisms," J. Immunol, 2000, pp. 6889-6895, vol. 165, http://www.jimmunol.org/content/165/12/6889.
Baker, S.P., et al., "The Injury Severity Score—A Method for Describing Patients with Multiple Injuries and Evaluating Emergency Care," The Journal of Trauma, 1974, pp. 187-196, vol. 14, No. 3.
Bandiera, G.W., "Evaluating Programs to Prevent Unintentional Trauma in Canada: Challenges and Directions," The Journal of Trauma, 1999, pp. 932-936, vol. 47, No. 5.
Boutoille, D., et al., "FITC-Albumin as a Marker for Assessment of Endothelial Permeability in Mice: Comparison with $^{125}$I-Albumin," Experimental Lung Research, 2009, pp. 263-271, vol. 35, No. 4.
Brun-Buisson, C., et al., "Risques et maîtrise des infections nosocomiales en réanimation : texte d'orientation SRLF/SFAR The risk for and approaches to control of nosocomial infections in ICUs: guideline from the SRLF/SFAR task force on nosocomial infections in ICUs," Réanimation, 2005, pp. 463-471, vol. 14, No. 6.
Cheadle, W. G., MD, et al., "HLA-DR Antigen Expression on Peripheral Blood Monocytes Correlates with Surgical Infection," The American Journal of Surgery, 1991, pp. 639-645, vol. 161, No. 6.
Damsgaard, C. T., et al., "Whole-blood culture is a valid low-cost method to measure monocytic cytokines—A comparison of cytokine production in cultures of human whole-blood, mononuclear cells and monocytes," Journal of Immunological Methods, 2009, pp. 95-101, vol. 340.
Ditschkowski, M., et al., "HLA-DR Expression and Soluble HLA-DR Levels in Septic Patients After Trauma," Annals of Surgery, 1999, pp. 246-254, vol. 229, No. 2.
Földes, G., et al., "Toll-like receptor modulation in cardiovascular disease: a target for intervention?", Expert Opin. Investig. Drugs, 2006, pp. 857-871, vol. 15, No. 8 [XP-002588741].
Göbel, A., MD, et al., "Injury Induces Deficient Interleukin-12 Production, But Interleukin-12 Therapy After Injury Restores Resistance to Infection," Annals of Surgery, 2000, pp. 253-261, vol. 231, No. 2.
International Search Report, Application No. PCT/EP2010/010111, Mar. 11, 2011, pp. 1-8.
Keel, M., MD, et al., "Endotoxin Tolerance alter Severe Injury and Its Regulatory Mechanisms," The Journal of Trauma: Injury, Infection, and Critical Care, 1996, pp. 430-437, vol. 41, No. 3.

(Continued)

Primary Examiner — Rodney P. Swartz
(74) Attorney, Agent, or Firm — Foley & Lardner LLP

(57) ABSTRACT

The present invention concerns a pharmaceutical composition comprising at least one agonist of at least one Toll Like receptor (TLR) chosen from TLR 4 and 9, for use in the prophylactic treatment of septic complications of post-traumatic systemic immunodepression in a patient who has suffered one or more severe traumatic injuries and is hospitalized in particular in an intensive care unit. Preferably, said TLR 4 agonist is monophosphoryl lipid A (MPLA) or deacylated 3-O-monophosphoryl lipid A (3D-MPLA) and said TLR 9 agonist is a CpG oligodeoxynucleotide (CpG ODN).

11 Claims, 11 Drawing Sheets

(56) References Cited

OTHER PUBLICATIONS

Figure 1:
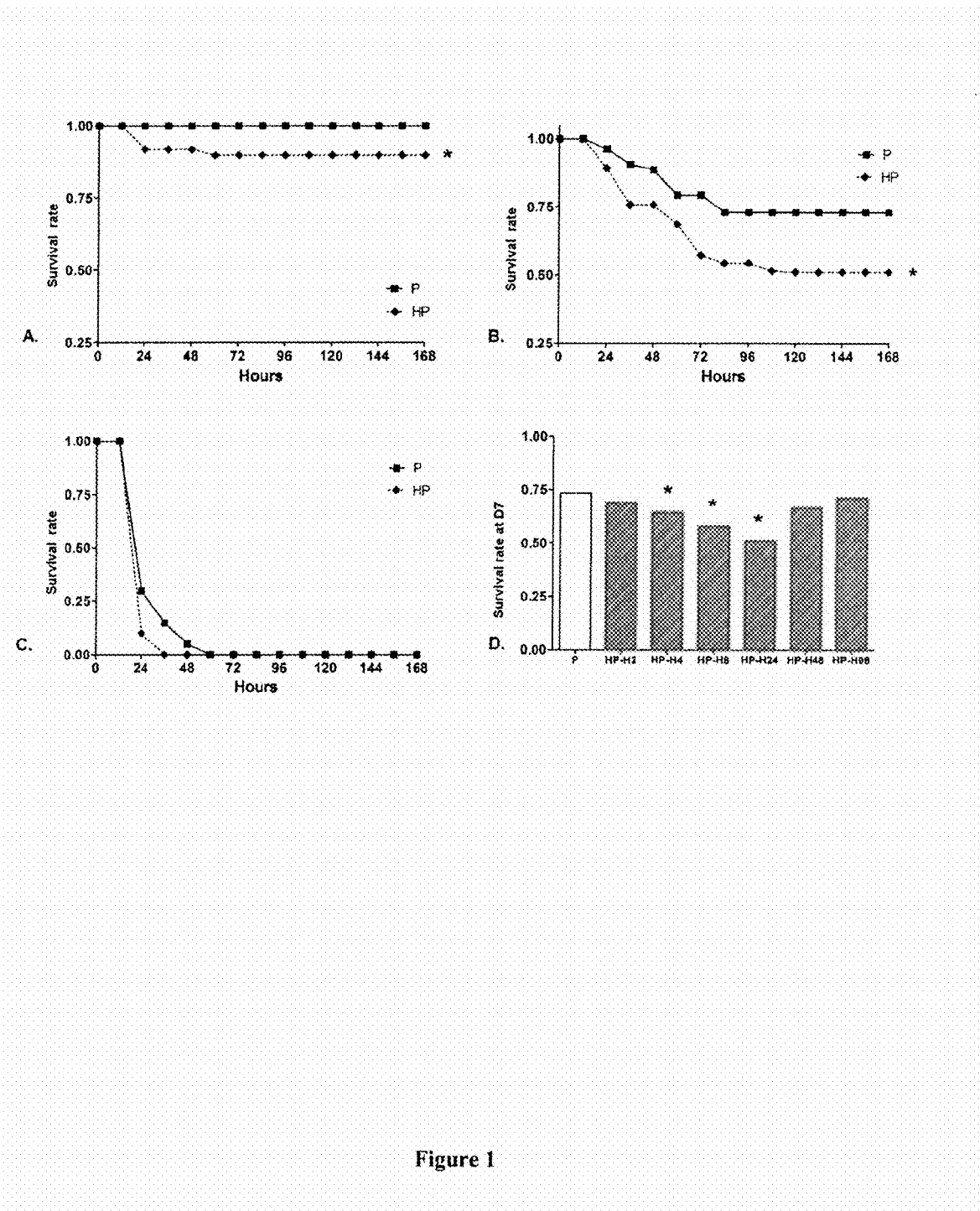

Kim, J. Y., et al., "HMGBI contributes to the development of acute lung injury after hemorrhage," Am J Physiol Lung Cell Mol Physiol., 2005, pp. L958-L965, vol. 288, No. 5.

Leonard, J. P., et al., "Phase I Trial of Toll-Like Receptor 9 Agonist PF-312676 with and Following Rituximab in Patients with Recurrent Indolent and Aggressive Non-Hodgkin's Lymphoma," Clinical Cancer Research, 2007, pp. 6168-6174, vol. 13.

Li, Y., et al., Hemorrhagic shock augments lung endothelial cell activation: role of temporal alterations of TLR4 and TLR2, Am J Physiol Regal Integr Comp Physiol, 2009, pp. R1670-R1680, vol. 297, [XP009135156].

Livak, K. J., et al., "Analysis of Relative Gene Expression Data Using Real-Time Quantitative PCR and the $2^{-\Delta\Delta C_T}$ Method." METHODS, 2001, pp. 402-408, vol. 25.

Mata-Haro, V., et al., "The Vaccine Adjuvant Monophosphoryl Lipid A as a TRIF-Biased Agonist of TLR4," SCIENCE, 2007, pp. 1628-1632, vol. 316.

Merad, M., et al., "Dendritic cell homeostatsis," BLOOD, 2009, pp. 3418-3427, vol. 113, No. 15.

Osborn, T., M., MD, et al., "Epidemiology of sepsis in patients with traumatic injury," Crit Care Med, 2004, pp. 2234-2240, vol. 32, No. 11.

Ouabed, A., et al., "Differential Control of T Regulatory Cell Proliferation and Suppressive Activity by Mature Plasmacytoid versus Conventional Spleen Dendritic Cells," J Immunol, 2008, pp. 5862-5870, vol. 180, No. 9.

Papia, G., et al., "Infection in Hospitalized Trauma Patients: Incidence, Risk Factors, and Complications," The Journal of Trauma: Injury, Infection. and Critical Care, 1999, pp. 923-927, vol. 47, No. 5.

PSR—Rapport de Recherche Preliminaire Partiel for Application No. FR 0906372, dated Jun. 30, 2010.

Rincón-Ferrari, M. D., MD, et al., "Impact of Ventilator-Associated Pneumonia in Patients with Severe Head Injury," The Journal of Trauma: Injury, Infection, and Critical Care, 2004, pp. 1234-1240, vol. 57, No. 6.

Rivkind, A. L., et al., "Neutrophil Oxidative Burst Activation and the Pattern of Respiratory Physiologic Abnormalities in the Fulminant Post-Traumatic Adult Respiratory Distress Syndrome," Circulatory Shock, 1991, pp. 48-62, vol. 33, No. 1.

Robinson, A., MD, et al., "Effects of hemorrhage and resuscitation on bacterial antigen-specific pulmonary plasma cell function," Critical Care Medicine, 1991, pp. 1285-1292, vol. 19, No. 10.

Sauaia, A., MD, et al., Epidemiology of Trauma Deaths: A Reassessment, The Journal of Trauma: Injury, Infection, and Critical Care, 1995, pp. 185-193, vol. 38, No. 2.

Spolarics, Z., MD, PhD, et al., Depressed interleukin-12-producing activity by monocytes correlates with adverse clinical course and a shift toward Th2-type lymphocyte pattern in severely injured male trauma patients. Critical Care Medicine, 2003, pp. 1722-1729 vol. 31, No. 6.

Stephan, R. N., MD, et al., "Mechanism of Immunosuppression following Hemorrhage: Defective Antigen Presentation by Macrophages," Journal of Surgical Research, 1989, pp. 553-556, vol. 46, No. 6.

Teasdale, G., et al., "Assessment of coma and impaired consciousness. A practical scale," Lancet, 1974, pp. 81-84, vol. 2.

Thobe, B. M., et al., "The Role of MAPK in Kupffer Cell Toll-Like Receptor (TLR)2-, TLR4-, and TLR9-Mediated Signaling Following Trauma-Hemorrhage," Journal of Cellular Physiology, 2007, pp. 667-675, vol. 210, XP-002588740.

Venet, F., PharmD, PhD, et al., "Decreased monocyte human leukocyte antigen-DR expression after severe burn injury: Correlation with severity and secondary septic shock," Critical Care Medicine, 2007, pp. 1910-1917, vol. 35, No. 8.

Wichmann, M. W., MD, et al., "Severe depression of host immune functions following closed-bone fracture, soft-tissue trauma, and hemorrhagic shock," Critical Care Medicine, 1998, pp. 1372-1378, vol. 26, No. 8.

Thobe et al., "The role of MAPK in Kupffer cell toll-like receptor (TLR) 2-, TLR4-, and TLR9-mediated signaling following trauma-hemorrhage," Journal of Cellular Physiology, vol. 210, No. 3, pp. 667-675, Mar. 2007.

Foldes et al., "Toll-like receptor modulation in cardiovascular disease: a target for intervention?," Expert Opinion on Investigational Drugs, vol. 15, No. 8, pp. 857-871, Aug. 2006.

Li et al., "Hemorrhagic shock augments lung endothelial cell activation: role of temporal alterations of TLR4 and TLR2," American Journal of Physiology, vol. 297, No. 6, pp. R1670-R1680, Dec. 1, 2009.

International Search Report issued in application No. PCT/EP2010/070111 on Mar. 11, 2011.

* cited by examiner

A.

B.

| | Control | Pneumonia | Haemorrhage – Pneumonia |
|---|---|---|---|
| Lactate (mmol/l) | 3.5±0.5 | 4.6±1.3 * | 6.0±1.5 *& |
| pH | 7.34±0.03 | 7.26±0.03 * | 7.22±0.01 *& |
| HCO3- (mmol/l) | 28.5±1.1 | 26.8±1.6 | 24.5±3.0 *& |
| BE (mmol/l) | +0.4±0.2 | -0.9±0.8 | -2.8±0.7 *& |
| PcO2 (kPa) | 6.4±1.1 | 3.4±1.2 * | 3.8±1.3 * |
| PcCO2 (kPa) | 7.3±0.9 | 8.5±0.7 | 9.1±1.3 |
| SvO2 (%) | 59±12 | 29±18 * | 35±19 * |
| Glycaemia (mmol/l) | 1.87±0.29 | 0.81±0.3 * | 1.36±0.23 *& |

TLR 4 AND 9 RECEPTORS AGONISTS FOR PREVENTING SEPTIC COMPLICATIONS OF POST-TRAUMATIC IMMUNODEPRESSION IN PATIENTS HOSPITALIZED FOR SEVERE TRAUMATIC INJURIES

The present invention relates to compositions and methods useful for preventing septic complications in hospitalized patients suffering from systemic immunodepression subsequent to one or more severe traumatic injuries.

More specifically, the present invention concerns a pharmaceutical composition comprising at least one agonist of at least one Toll Like receptor (TLR) chosen from among TLR 4 and 9, for use in the prophylactic treatment of septic complications of post-traumatic systemic immunodepression in a patient who has suffered one or more severe traumatic injuries and is hospitalized, in particular in an intensive care unit. Preferably, said TLR 4 agonist is monophosphoryl lipid A (MPLA) or 3-O-deacylated monophosphoryl lipid A (3D-MPLA) and said TLR 9 agonist is a CpG oligodeoxynucleotide (CpG ODN).

In France and the United States, severe traumatic injury is the leading cause of mortality during the first thirty years of life, and more globally the fourth cause of death with more than 160 000 and 10 000 deaths each year, respectively (Mathers et al. 2006; Patton et al. 2009). If mortality directly related to the traumatic injury itself is set aside, secondary post-traumatic mortality is essentially due to a specific, severe and prolonged systemic immunodepression (SI) (Keel et al. 1996). Physiological response to trauma is based on a complex neurohumoral activation. Deregulation of cell-mediated immunity is responsible for an immune deregulation (Keel et al. 1996; Ditschkowski et al. 1999). Haemorrhagic shock is a major cause of this immune disorder on account of the extent of ischaemic lesions (tissues deprived of oxygen during the ischaemic phase (bleeding)) and reperfusion (massive release of toxic compounds and of inflammation mediators during resuscitation of the injured person) (Stephan et al. 1989). In addition, tissue lesions act in synergy with haemorrhage causing highly specific modulation of the immune response of traumatized patients (Wichmann et al. 1998). In the very particular case of patients hospitalized for severe trauma or polytrauma, the post-traumatic SI that characterizes these patients is directly responsible for septic complications, generally of secondary infections acquired in the hospital environment (or nosocomial infections).

Post-traumatic SI and its associated septic complications are therefore two priority targets if it is desired to improve the future prognosis of patients with severe traumatic injury since the human and economic cost of post-traumatic infectious complications remains considerable. Indeed, infections are the prime cause of secondary mortality in heavy traumatology. The onset of infection in a patient with severe traumatic injury raises predicted mortality from 7 to 21%, increases on average the hospital stay in intensive care from 5 to 21 days and extends hospitalization from 7 to 34 days (Rincon-Ferrari et al. 2004; Papia et al. 1999). For example, the overall additional cost related to ventilator-associated pneumonia (VAP) in France is estimated at 800 million euros per year. Finally, according to a WHO report published in 2005, the cost of treating 5 nosocomial infections of average severity is equivalent to the entire annual budget planned for the purchase of hand hygiene products in a hospital department.

This translates, firstly, as the inefficacy of current means for preventing nosocomial infections in this particular population of patients, and, secondly, as the medico-economic importance of this public health issue (SFAR 2005).

Antigen-presenting alterations are a major cause of sepsis following after severe traumatic or poly-traumatic injury. Antigen-presenting capacities have been researched with regard to acute stress, in particular septic or traumatic stress. These studies essentially concerned the expression of HLA-DR on blood monocytes. In patients suffering from serious traumatic injury, it has been shown that the monocyte membrane expression of HLA-DR is significantly lower than the one observed in healthy volunteers (Venet et al. 2007). Ditschkowski et al. (1999) studied the monocyte membrane expression of HLA-DR in 66 patients with severe multiple trauma over the first 14 days of hospitalization. The twenty patients who developed sepsis during their recovery showed, as from D0 and up to D14, a strong reduction in the expression of monocyte HLA-DR compared with the 46 multiple trauma patients who did not suffer any infection throughout their hospital stay. Diminished expression of HLA-DR has also been reported in surgery patients and, once again, this finding is accompanied by an increase in septic complications and in excess mortality in these patients (Ditschkowski et al 1999). In the light of this data, it appears that, very soon after traumatic injury, there is a deactivation phase of the immune system marked by a reduction in the antigen-presenting capacity of the monocytes (diminished HLA-DR expression). It is precisely this highly specific disorder of the immune system in patients, consecutively to a severe traumatic or to a poly-traumatic injury which fosters the onset of nosocomial infections and is correlated with a worring surmortality.

At the present time, the physiopathology of severe traumatic injury and of its secondary complications remains based on exclusive clinical considerations. Yet the Inventors are the first to propose an original approach taking into account the physiological and pathological condition, particularly the immunological condition, of patients suffering from severe traumatic injury. As described in detail below, the Inventors have developed the first animal model reproducing post-traumatic SI observed in human, and combined with pneumonia, to mimic the human pathology in the most realistic manner possible. Through their work, conducted in particular with the help of this animal model, the Inventors have managed to explain the incidence of septic complications of post-traumatic SI in patients hospitalized for severe traumatic injury, and propose for the first time adapted and efficient means for preventing these complications.

Over the last ten years or so and following the discovery of TLRs, innate immunity has become a particularly widespread subject of research. Innate immunity provides an highly efficient, specific anti-infection defence, which is most often sufficient to eradicate a site of infection. The study of innate immunity has allowed the discovery that it is capable of highly specific recognition of conserved pathogen-associated molecular patterns (PAMPs) of numerous pathogens, essentially via TLRs belonging to the family of Pattern Recognition Receptors (PRRs).

PAMPs have various origins (bacteria, viruses, parasites, etc.) and are of varied type (protein, sugar, nucleic acid, etc.). In structural terms, TLRs are type 1 transmembrane proteins comprising an extracellular receptor domain of the danger signal and composed of numerous leucin-rich repeats (LRRs), a transmembrane domain and an intracellular domain containing a domain allowing the transduction of the activation signal (called <<death domain>>). TLRs are largely expressed by numerous types of cells, for example blood cells, cells of the spleen, lungs, muscles, intestines, etc. TLRs, particularly in mammals, represent key proteins allowing the detection of an infection and the triggering of a suitable immune response. Most mammalian species have between 10 and 15 types of TLRs. In particular, 13 TLRs (TLR 1 to TLR 13) have been identified in mice, and 10 in man. Each TLR is capable of specifically recognizing certain PAMPs. For example, the natural ligands of the TLR 4 receptor include the LPS of the bacterial wall and glycoproteins of viral origin. With regard to the TLR 9 receptor, this receptor recognizes the non-methylated CpG islands of bacterial and viral DNA.

TLRs and their agonists therefore appear to be major targets for the research and development of efficient therapies in the area of combatting infections.

Among the known TLRs agonists, particular mention may be made of MPLA and CpGs. MPLA, or monophosphoryl lipid A, is a non-toxic derivative of lipopolysaccharide (LPS) originating from a strain of *Salmonella minnesota*. It essentially acts via TLR 4. In structural terms, MPLA and deacylated 3-O MPLA (or 3D-MPLA) have a sugar backbone on which long chain fatty acids are attached. They are highly hydrophobic molecules. MPLA and 3D-MPLA are conventionally used as immune adjuvants associated with antigen preparations in vaccines for the prevention of infections (for example, against the influenza virus) or therapeutic vaccines for the treatment of cancers and chronic infections (see for example European patent EP 0 971 739).

CpG patterns are short, single-strand DNA molecules containing a cytosine <<C>> followed by a guanine <<G>>. The letter <<p>> in the acronym <<CpG>> designates the phosphodiester backbone of DNA. Synthetic CpG oligodeoxynucleotides (or CpG ODNs) differ from microbial CpG ODNs by their backbone that is partially or fully modified to phosphorothioate <<PS>> (instead of phosphodiester) and by a polyG tail at their 5' and/or 3' terminal end(s). PS modification prevents the degradation of CpG ODNs by nucleases and the polyG tail improves management by cells. Natural CpGs are particularly abundant in microbial genomes and much rarer in vertebrates. They are exclusively recognized by TLR 9. Non-methylated CpGs are used in vaccine compositions as adjuvants (see for example European patent EP 0 772 619).

Immunostimulating compositions comprising one or more ligands of TLRs have already been proposed for therapeutic and/or prophylactic purposes. For example, international application WO 2009/088401 proposes improving the immune response of an individual using such compositions. Compositions including CpGs and/or MPLA are thus for administration to an individual presenting, within an undefined future, a higher risk than normal of developing an infection, cancer or allergy. Anti-infection applications envisaged in this application are purely vaccine-related: the purpose is effectively to immunize an individual for protection against an infectious agent to which such individual may be exposed during their lifetime. Yet typically, in the area of vaccine-therapy, nobody knows: (i) whether the vaccinated individual will effectively be exposed during his or her lifetime to the infectious agent against which he or she is supposed to be protected; (ii) assuming that such individual will be exposed to the infectious agent, when such exposure will occur; (iii) whether the vaccinated individual is efficiently protected so as to not suffer an infection in the event of exposure to the infectious agent; and (iv) assuming that protection is associated with the vaccine, the actual length of time of this protection with regard to exposure to the infectious agent. In addition, the teaching contained in application WO 2009/088401 is insufficient to show the efficacy of the described vaccine compositions.

On the contrary, in the present invention, firstly, the proposed compositions are not vaccinal in the conventional meaning of the term, and, secondly, the population to be treated is highly specific. Infections to be prevented in the present invention are septic complications following post-traumatic systemic immunodepression in patients hospitalized for severe traumatic injury. The onset of these complications is only likely to occur within a well-defined time period starting from the day of traumatic injury. In addition, the present invention targets a very particular category of patients, whose physiological and pathological condition, immunological in particular, differs from the one of the population targeted by standard vaccination. As indicated in the foregoing, the patients targeted here are ill; they suffer from one or more severe traumatic injuries, whereas the population of a vaccination campaign is generally healthy. The pathological condition of the patients targeted here is not banal from this viewpoint as it warrants management and monitoring by skilled medical teams, and requires an emergency hospitalization, relatively long-term, typically in one or several specialized hospital units (intensive care, heavy traumatology . . . ). As indicated above, these patients suffer from specific, severe and prolonged post-traumatic SI which is a direct consequence of the severe traumatic injury or injuries they have suffered. The characteristics particular to post-traumatic SI and to the septic complications associated therewith are detailed in the following description.

The subject of the present invention is therefore a pharmaceutical composition comprising at least one agonist of at least one TLR chosen from TLR 4 and 9, for use in the prophylactic treatment (or prevention) of septic complications of post-traumatic systemic immunodepression in a hospitalized patient suffering from one or more severe traumatic injuries.

The invention targets a very particular patient population. The patients under consideration suffer from one or more severe traumatic injuries. To simplify, the term <<seriously traumatized patients>> or <<severely traumatized patients>> may be used. Preferably, the patients under consideration have at least two traumatic injuries among which at least one injury is life-threatening (i.e. it may be fatal over the short term). Further preferably, the severely traumatized patients have an injury severity score (ISS) of at least 16. For highly severe traumatic injuries, the ISS score is of at least 25. Calculation of the ISS score takes into account the injuries to several regions of the patient's body (head and neck; face; thorax; abdomen and pelvis; pelvic girdle and limbs; skin and sub-cutaneous tissues). The extent of injury of each region is scored from 1 to 6 depending on its severity (1: minor injury, 6: critical injury). The ISS is then calculated by squaring the score of the three most severely injured regions (for example if the scores for each region are the following: head 4, abdomen 3, thorax 2, other regions 1, then the ISS score will be $4^2+3^2+2^2=16+9+4=29$ (Baker et al. 1974)). Alternatively or additionally, the traumatized patients considered in the present invention have a severe brain injury as defined by the Glasgow scale (CGS) score of less than 8. The determination of the CGS score is a method which allows assessment of coma depth by examining the variability of 3 very precise clinical criteria which are: 1) opening of the eyes (score of 1: none, to 4: spontaneous opening of eyes) 2); motility (ability to move) or if preferred best motor response (scored from 1: none, to 6: adapted movements) and 3) response to questions asked (verbal response scored from 1: none, to 5: oriented answer). The CGS score is the sum of the results obtained for the three above-mentioned clinical criteria. The minimum is therefore 3 and the maximum 15 (Teasdale et al, 1974).

As explained above, the particular patient population targeted by the invention differs by a highly specific post-traumatic SI.

This post-traumatic SI is preferably characterized by:
a) a decrease in the ex vivo production level of pro-inflammatory cytokines induced by white blood cells after stimulation by LPS of gram negative bacilli, e.g. *Escherichia coli*, compared with the production level observed in a healthy individual; and/or
b) a decrease in the expression level of HLA-DR on the antigen-presenting cells of patients, compared with the expression level observed in a healthy individual.

These characteristics of post-traumatic SI have been confirmed in the literature (Keel et al. 1996; Spolarics et al. 2003; Cheadle et al. 1991). The observed decrease in the cytokine production level (expressed for example in picograms/ml) is determined in comparison with healthy volunteers whose cytokine production level represents a value of 100%. Cytokines are typically measured in the cultures of whole blood stimulated by LPS (in general of *Escherichia coli*). The HLA-DR expression is defined in relation to healthy volunteers, either as per the number of HLA-DR molecules expressed on the cells surface (Mean Fluorescence Intensity—MFI), or as a percentage, the value of 100% representing the HLA-DR expression level in healthy volunteers. In particular, if a percentage comparison is used, the decrease at a) and/or b) above is at least of about 20%. It is preferably of at least about 25%, further preferably of at least about 30, 35, 40, 45% and still further preferably of at least about 50, 55, 60%, even higher.

Further preferably, the post-traumatic SI observed in patients with severe traumatic injuries is such that the HLA-DR expression level on monocytes of said patients within 24 hours following traumatic injury or injuries (from D0 to D1) is diminished relative to the expression level observed in a healthy individual. This initial decrease may also, in practice, allow prediction of the risk of septic complications (or secondary infections). Thus, a low HLA-DR expression level on monocytes on the first day following severe traumatic injury or injuries (D1), for example a decrease of 50%, is predictive of a high risk that the patient will contract a secondary infection. HLA-DR expression is expressed versus healthy volunteers, i.e. either as the number of HLA-DR molecules expressed on the cells surface (MFI—Mean Fluorescence Intensity), or as a percentage, the value of 100% representing the level of HLA-DR expression in healthy volunteers. In particular, if a percentage comparison is used, the decrease in HLA-DR expression level is of at least about 20%, preferably of at least about 25%, further preferably of at least about 30, 35, 40, 45% and still further preferably of at least about 50, 55, 60%, even higher.

In the light of the preceding paragraphs, the person skilled in the art will easily understand that the pathological condition of the particular patient population targeted by the present invention can necessarily and sufficiently be defined by the above-mentioned characteristics. This pathological condition and the risks of septic complications associated therewith occur within a limited, fully specific time scale, following the traumatic injury or injuries which led said patients to a hospital intensive care unit. In particular, the post-traumatic systemic immunodepression under consideration in the present invention involves anti-inflammatory mechanisms and in this respect differs from pathological conditions involving pro-inflammatory reactions of SIRS type, notably with regard to sepsis.

The septic complications (or secondary infections) whose prevention is made possible by the pharmaceutical composition subject of the present invention are more particularly nosocomial infections, notably bacterial. In particular, the bacterial infections involved are those chosen from among pneumonia such as VAP, urinary infections, central venous catheter-related infections, cerebral-meningeal bacterial infections such as empyema meningitis and brain abscesses. More particularly, pneumonia infections are due to pathogenic bacteria chosen from staphylococci, preferably *Staphylococcus aureus*, further preferably methicillin-sensitive *Staphylococcus aureus, Haemophilus* sp., preferably *H. influenzae*, pneumococci, enterobacteria, *Pseudomonas* sp., in particular *P. aeruginosa*. Pneumonia-causing bacteria may also belong to other bacterial genii or species (e.g. gram negative bacilli and gram positive cocci). In addition, they may be resistant to antibiotics. For infections other than pneumonia, bacteria which may be responsible may be gram negative bacilli (e.g. *E. coli, Proteus mirabilis, Pseudomonas aeruginosa*) and gram positive cocci (e.g. *S. aureus*) for urinary infections; gram negative bacilli (e.g., *E. coli, P. mirabilis, P. aeruginosa*), gram positive cocci (e.g., *S. aureus*, negative coagulase staphylocci) and yeasts such as *Candida* sp. for infections on central catheters; gram negative bacilli (e.g., *E. coli, P. mirabilis, P. aeruginosa*) and gram positive cocci (e.g., *S. aureus*, negative coagulase staphylococci, *Streptococcus pneumoniae*) for cerebral-meningeal bacterial infections.

It will be understood that, in the pharmaceutical composition of the present invention, the TLRs agonist(s) is(are) present in an effective quantity (or pharmaceutically effective quantity). This means that the quantity of agonists in the composition is such that, once administered, the composition is capable of preventing septic complications of post-traumatic systemic immunodepression in hospitalized patients suffering from one or more severe traumatic injuries.

Preferably, the pharmaceutical composition of the present invention comprises at least one TLR 4 agonist and at least one TLR 9 agonist.

The term <<agonist>> here designates any molecule or combination of molecules which stimulates a receptor. For example, a TLR agonist may be a TLR ligand, an analogue or derivative of said ligand.

By <<molecule or combination of molecules stimulating a TLR receptor>> is meant herein molecules which, via said TLR, trigger (directly or indirectly) a specific intracellular signalling cascade. This signalling cascade involves numerous adaptor proteins such as MyD88, MAL, TRIF and TRAM. According to the present invention, TLR4 and TLR9 agonists both activate the MyD88 signalling pathway. However, TLR4 agonists also use the proteins MAL, TRIF and TRAM, which is not the case for TLR9 agonists.

The recruiting of these adaptor proteins leads inter alia to activation of macrophages and dendritic cells (DCs), and to the production of pro-inflammatory cytokines, chemokines and immunoglobulins. TLR4 agonists more particularly activate the macrophages and myeloid dendritic cells, whilst TLR9 agonists activate the macrophages, the plasmacytoid dendritic cells (pDCs) and B lymphocytes.

A TLR ligand may be of chemical (e.g. MPLA) or biological type (e.g., a foreign compound recognized by the immune system as non-self, such as the nucleic acids of bacteria, fungi or viruses, and more particularly the deoxyribonucleic acid of *Candida albicans* or CpGs). Analogues or derivatives of TLRs ligands are notably structurally modified ligands (e.g., mutated if they are biological molecules, or structurally modified if they are chemical molecules), mimetic peptides, and more generally any molecule or combination of molecules capable of carrying out the biological function of the ligand which is to stimulate the receptor.

Preferably, the TLR4 agonist contained in the composition of the invention is monophosphoryl lipid A (MPLA) or 3-O-deacylated monophosphoryl lipid A (3D-MPLA). Particular use is made of MPLA.

Preferably, the TLR 9 agonist contained in the composition of the invention is a CpG oligodeoxynucleotide (CpG ODN). Preferred use is made of a synthetic CpG ODN of at least 8 nucleotides containing at least one non-methylated CpG dinucleotide. Preferably, a CpG ODN containing no more than 100 nucleotides is used. Further preferably, the CpG ODN used in the composition of the present invention contains from 8 to 40 nucleotides. The person skilled in the art will choose the suitable CpG ODN or ODNs among the phosphodiesters or the phosphodiesters having one or more phosphorothioate modifications (phosphodiester/phosphorothioate), or the phosphorothioates. Preference is given to the use of phosphodiester/phosphorothioate CpG ODNs, or phosphorothioates. Advantageously, CpG ODNs devoid of palindromic sequences with about 4 to 8 nucleotides are used. It may be chosen to use a CpG ODN other than CpG 7909 (or PF-3512676) described in Leonard et al. (2007).

Preferably, the pharmaceutical composition of the invention further comprises one or more excipients or additives or pharmaceutically acceptable carriers. For example, the composition of the present invention may comprise one or more agents chosen from diluents, anti-foaming agents, stabilizers, colouring agents, preserving agents, etc. Preferred use is made of inert agents, meaning that in the compositions subject of the invention, the only active agents from the viewpoint of the prophylactic treatment sought after here, are the TLRs agonist(s). Nonetheless, the pharmaceutical composition subject of the present invention may comprise one or more antigens, in addition to said TLRs agonists. The antigen(s) thus associated with the TLRs agonist(s) will allow the obtention of a powerful immunostimulation specific to the antigen(s) added to the pharmaceutical composition of the invention. The antigen(s) optionally used are mainly bacterial antigens, in particular antigens of pathogenic bacteria such as staphylococci, preferably Staphylococcus aureus, further preferably methicillin-sensitive *S. aureus, Haemophilus* sp., preferably *H. influenzae*, pneumococci, enterobacteria, *Pseudomonas* sp., in particular *P. aeruginosa*. The antigens may derive from other bacterial genii or species depending on the infections it is desired to prevent (for example gram negative bacilli such as *E. coli, Proteus mirabilis*, etc., gram positive cocci such as *Streptococcus pneumoniae*, and yeasts such as *Candida* sp.).

Advantageously, the composition of the present invention is administered to patients, for example by injection, starting from about 12 h, preferably from about 24 h, after their admission to hospital, in particular in an intensive care unit. In particular, the composition is administered after stabilization of the clinical condition of the patients. In general a patient is stabilized when, depending on the type(s) of injuries suffered, bleeding has been brought under control and/or short-term life-threatening injuries have been given emergency surgical treatment. In practice, a patient is said to be <<stabilized>> if the vital functions (essentially circulatory and respiratory) are stable.

The composition of the present invention is preferably administered one or several times if necessary, over a period of no more than about 1 month, preferably no more than 28 days, as from the date of admission of the patients to hospital, in particular in an intensive care unit. In other words, the septic complications it is desired to prevent are likely to occur (or to be contracted) over a period of no more than about 1 month, preferably of no more than 28 days, as from the date of admission to hospital of the patients. For example, it was ascertained that septic complications occurred in 40 to 50% of patients with severe traumatic injury between D0 and D10, and in an additional 10 to 20% of patients between D10 and D28, i.e. a total of 50 to 70% of patients contracted a secondary infection (Osborn et al., 2004).

In particular, the pharmaceutical composition subject of the present invention can be administered one or more times during the period in which patients are intubated.

Therefore, the invention also relates to a prophylactic method for treating septic complications or post-traumatic immunodepression in hospitalized patients suffering from one or more severe traumatic injuries, whereby said patients are administered a pharmaceutical composition such as described above.

A further subject of the present invention is the use of at least one agonist of at least one TLR chosen from TLR 4 and 9, to prepare a medicinal product intended for the prophylactic treatment of septic complications of post-traumatic systemic immunodepression in a hospitalized patient suffering from one or more severe traumatic injuries.

Preferably the said medicinal product is a pharmaceutical composition conforming to the preceding description.

The present invention is illustrated by the following figures:

FIG. 1: Pilot study on effects of the inoculum and of the time interval between haemorrhaqic shock and methicillin-sensitive *Staphyloccocus aureus* (or <<MSSA>>) on mortality in mice.

Two groups of mice were studied: HP group (haemorrhagic shock followed by MSSA pneumonia) and P group (MSSA pneumonia alone). Data are expressed as a percentage and represent three independent experiments, each having the same statistical significance—A.B.C. Effect of the inoculum on mortality. Twenty-four hours after haemorrhage, infection with pneumonia was caused using $7\times10^6$ CFU (A.) or $7\times10^6$ CFU (B.) or $7\times10^7$ CFU (C.) of MSSA (HP group) and compared with a group of mice with pneumonia alone (P group). The survival rate of each group was controlled twice a day for 7 days (168 hours). Each group comprised 15 mice (*$p\leq0.05$ versus group P). D. Effect of time of onset on mortality. Mortality was evaluated in mice subjected to a MSSA pneumonia ($7\cdot10^6$ CFU) caused 2, 4, 8, 24, 48 and 96 hours after haemorrhage (HP-H2, -H4, -H8, -H24, -H48 and -H96, respectively) and compared with a group of mice subjected to MSSA pneumonia alone (P group). Each group comprised 15 animals. (*significantly different from P group after Bonferroni correction).

Figure 2:
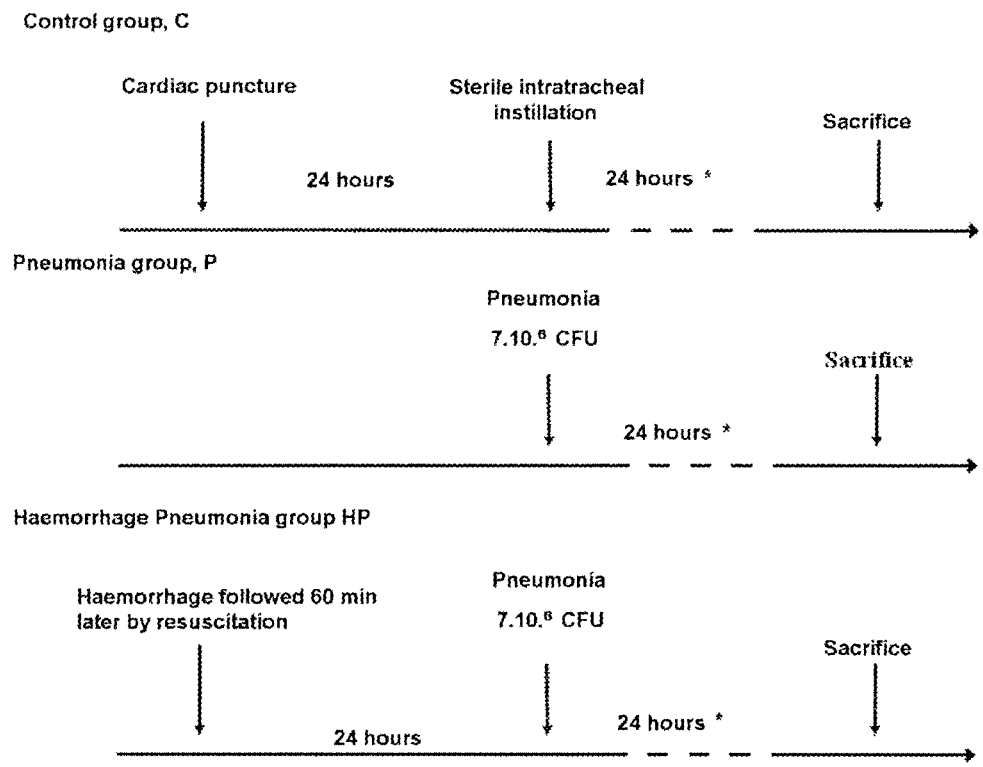

FIG. 2: Schematic illustration of the 3 groups in the main study.

C: control group; P: Pneumonia group; HP: Haemorrhage Pneumonia group.

Figure 3:
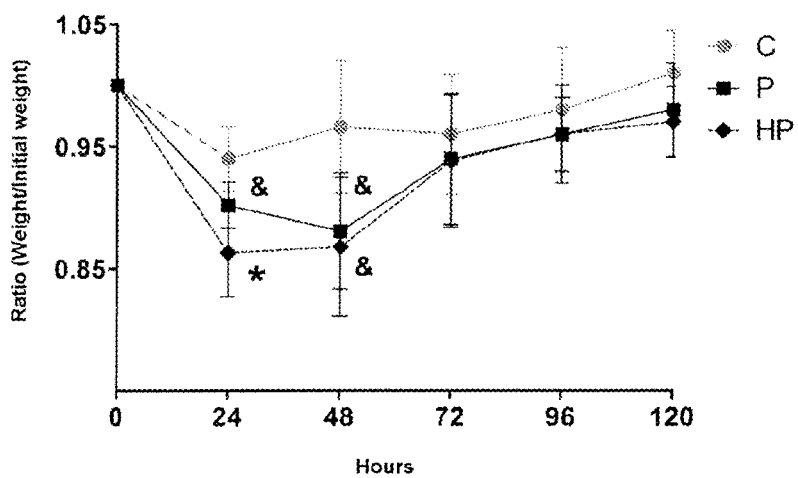

FIG. 3: Haemorrhagic shock aggravates weight loss and the biological consequences of MSSA pneumonia.

Data are expressed as the median +/−SEM and are representative of three independent experiments each having the same statistical significance. A. The mice were weighed every day for 5 days (120 hours). Each group comprised 10 mice (& $p\leq0.001$ versus group C, *$p\leq0.01$ versus group P). B. Blood samples were taken from the right atrium 24 hours after the onset of pneumonia. Each group comprised 5 animals. (*$p\leq0.05$ versus group C, & $p\leq0.05$ versus group P).

Figure 4:
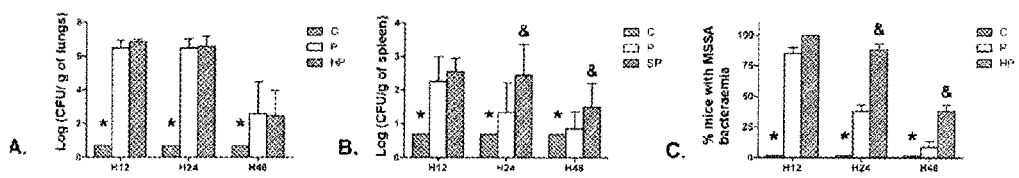

FIG. 4: Post-haemorrhagic SI induces bacteraemia during MSSA pneumonia.

The animals were sacrificed 12, 24 and 48 hours after the onset of pneumonia. MSSA colony counts in the lungs and spleen were conducted after culture in a selective medium.

The data presented include 15 mice per group grouping together 3 independent experiments, each having the same statistical significance (*p≤0.05 versus all the others; & p≤0.05 versus group P at the indicated time).

Local (A) and systemic (B.C.) development of the bacterial inoculum. The data given are expressed as the median±SEM (A.,B.) or as a percentage±SEM (C.). The detection threshold of the method was 0.7 CFU per gram of tissue.

Figure 5:
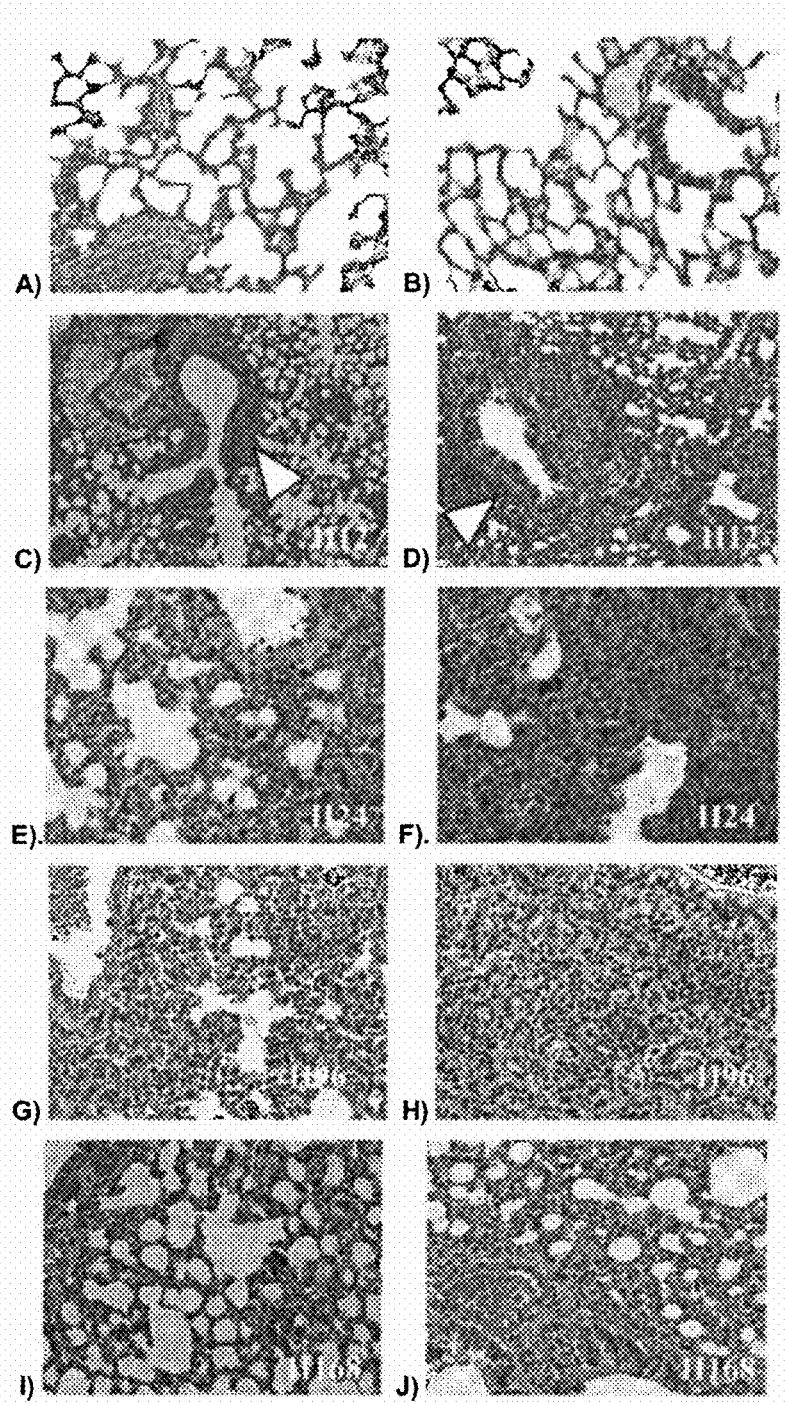

FIG. 5: Post-haemorrhagic SI exacerbates the histological lesions of MSSA pneumonia.

Four groups of mice were studied: Naive; Control (C group); MSSA pneumonia alone (P group) and with haemorrhage followed by MSSA pneumonia (HP group). The tissues fixed in formaldehyde were cut and stained with hematoxylin and eosin before microscopic analysis (magnification ×20).

Histological appearance representing the lungs of naive mice (A.) with healthy lung; (B) mice in the control group at the 24$^{th}$ hour. Pulmonary parenchyma was then evidenced by a series of images obtained in animals at different times of the pneumonia: 12, 24, 96 and 168 hours (C.E.G.I.) for P group; and (D.F.H.J) for HP group. Aggregates of immune cells were seen on and after the 12$^{th}$ hour of infection (arrows) and were more numerous in the HP group than in the P group at all time periods.

Figure 6:
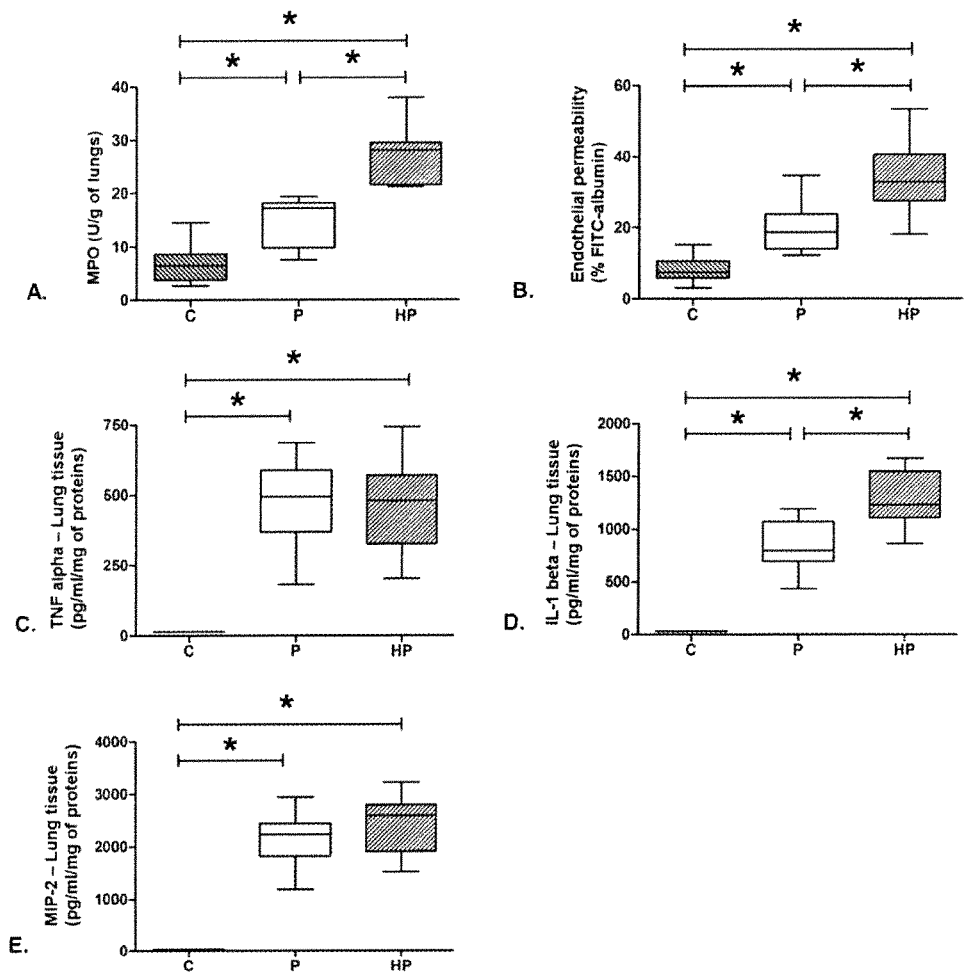

FIG. 6: Post-haemorrhagic SI aggravates the inflammatory lesions of MSSA pneumonia.

Each group of mice comprised 5 animals. Data are expressed as the median±25-75$^{th}$ percentiles and are representative of three independent experiments each having the same statistical significance. (*p≤0.05).

A. Accumulation of polynuclear neutrophils in the lungs. Myeloperoxidase activity (MPO) was measured in both lungs.

B. Pulmonary endothelial lesions. Endothelial permeability was determined by measuring the FITC-albumin percentage passing through the pulmonary capillaries.

C.D.E. Pulmonary concentrations of cytokines. Concentrations of TNF-alpha (C.), IL-1 beta (D.) and MIP-2 (E.) were measured in lung homogenates.

Figure 7:
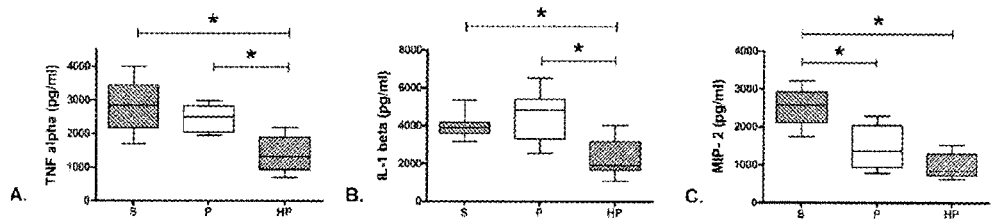

FIG. 7: Post-haemorrhagic SI increases blood hypo-reactivity to LPS during MSSA pneumonia.

A sample of whole blood was cultured 24 hours with LPS derived from *E. coli* O111B4 and cytokines were measured in the supernatants of the cell cultures. Each group comprised 5 animals. Data are expressed as the median±25-75$^{th}$ percentiles and are representative of three independent experiments, each having the same statistical significance. (*p≤0.05).

Concentrations of TNF-alpha (A.), IL-1 beta (B.) and MIP-2 (C.) in the cell cultures non-stimulated with LPS were all below the dosage detection threshold.

Figure 8:
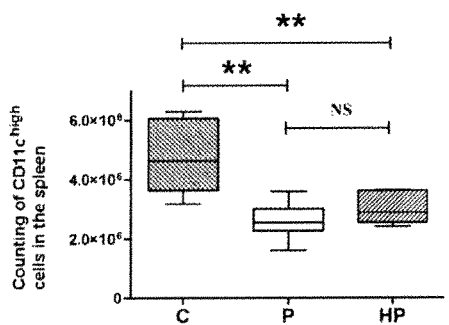
Figure 8:
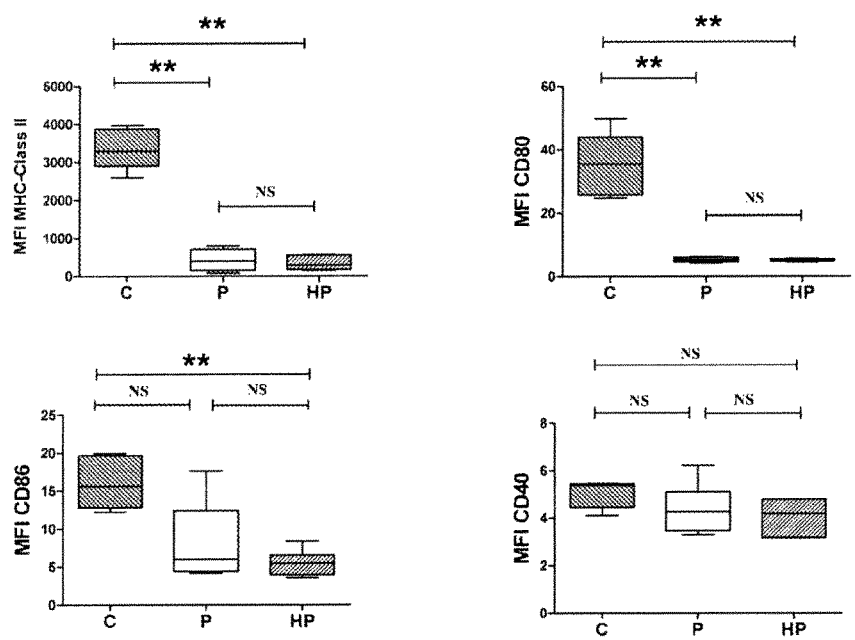

FIG. 8: Number and maturation state of splenic CD11c$^{high}$ cells during MSSA pneumonia whether or not preceded by haemorrhagic shock.

Each group of mice comprised 6 animals. Data are expressed as the median±25-75$^{th}$ percentiles and are representative of two independent experiments, each having the same statistical significance (**p≤0.01).

A. Counting of CD11c$^{high}$ cells in the spleen. In each group, the cell suspension obtained by enzymatic digestion of spleens was followed by a count after which the percentage of CD11c$^{high}$ cells was determined by FACS. The absolute number of CD11c$^{high}$ cells was then calculated.

B. Expression of CD11c$^{high}$ maturation markers. The following membrane markers were analyzed using FACS: MHC-Class II, CD40, CD80, CD86.

Figure 9:
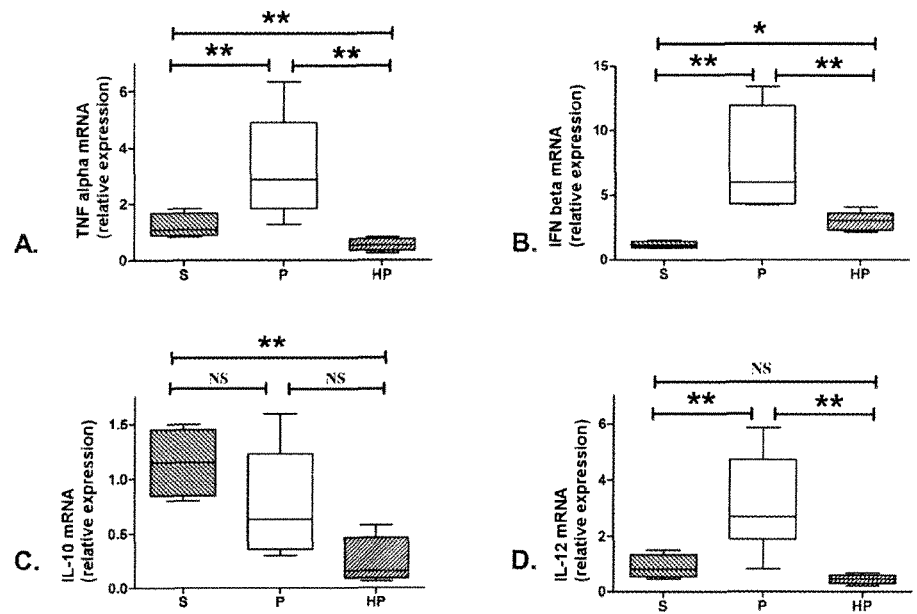

FIG. 9: Post-haemorrhagic SI reduces the transcription: (A.) of a cytokine dependent on Nuclear Factor-kB (NF-kB), (B.) of a cytokine dependent on Interferon Regulatory Factor (IRF-7), (C.) of Interleukin (IL-10) and (D.) of IL-12 in splenic DCs following after MSSA pneumonia.

Each group of mice comprised 6 animals. Data are expressed as the median±25-75$^{th}$ percentiles and are representative of two independent experiments, each having the same statistical significance (*p≤0.05; **p≤0.01).

A. B. C. D. RT-PCR quantitative analysis of (A.) Tumor Necrosis Factor (TNF alpha) mRNA; (B.) Interferon (IFN beta) mRNA; (C.) IL-10 mRNA and (D.) IL-12 mRNA in splenic DCs. The mRNAs were extracted from the CD11c+ cells positively selected in the splenic cell suspensions.

Figure 10:
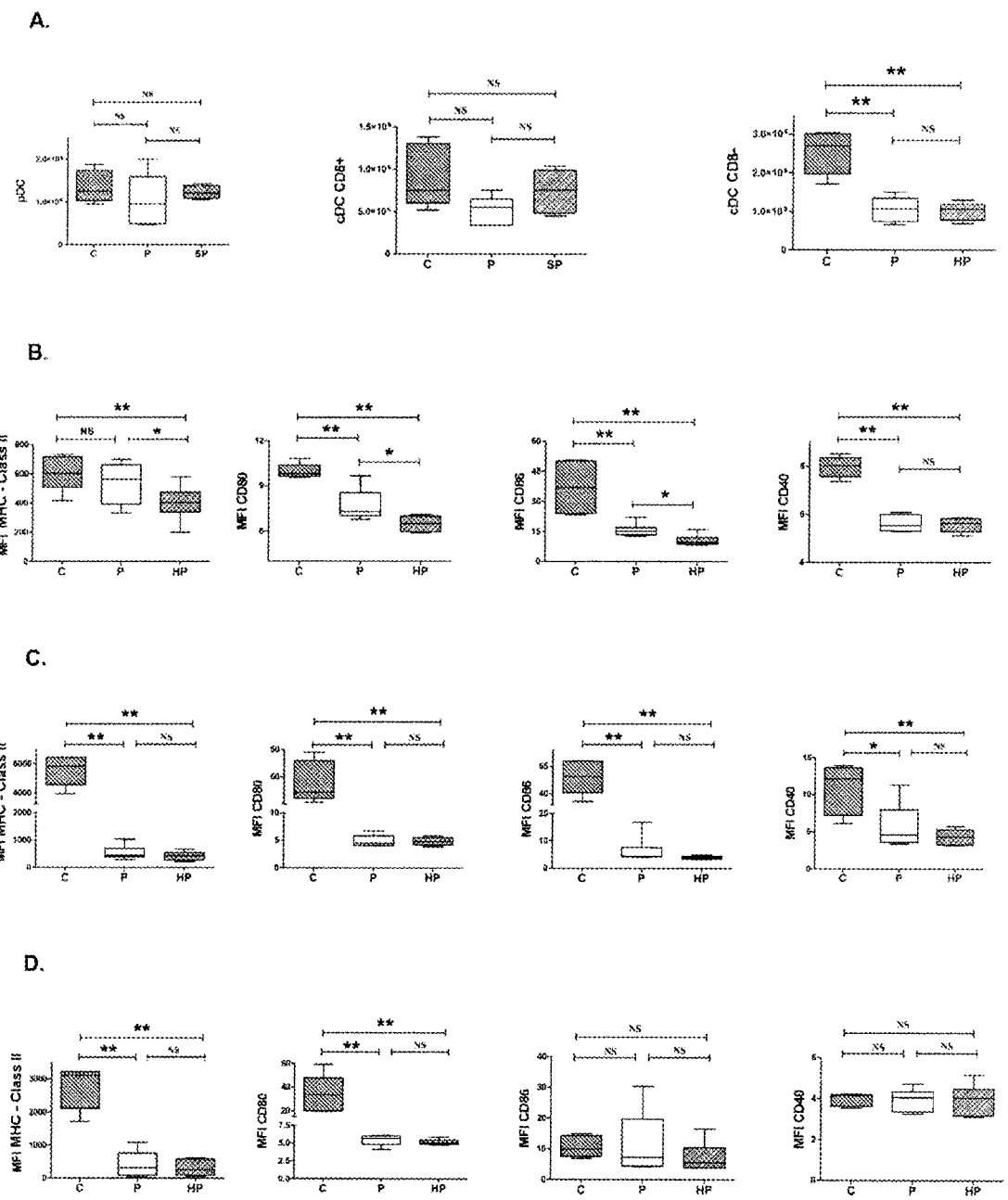

FIG. 10: Alterations of the phenotypes of dendritic cell subsets related to post-haemorrhagic SI during MSSA pneumonia.

Each group of mice comprised 6 animals. Data are expressed as the median±25-75$^{th}$ percentiles and are representative of two independent experiments each having the same statistical significance (*p≤0.05; **p≤0.01).

Number of cells of each subset of splenic DCs (A.), Antigen-presenting capacities of the antigen and maturation state of pDCs (B.) ; of conventional DCs, cDCs: CD8$^+$ cDCs (C.) and CD8$^−$ cDCs (D.) in the spleen following a MSSA pneumonia. Count of splenic DC subset. The cells were obtained after enzymatic digestion of the spleens. Counting on Malassez cell followed by determination of the percentage of each cell type was performed using FACS. The DC subsets were defined by their following membrane markers: B220 and SyglecH for pDCs, CD11c$^{high}$ and CD8$^{high}$ for CD8$^+$ cDCs; CD11c$^{high}$ and CD8$^{low}$ for CD8$^−$ cDCs. Expression of DC maturation markers. The following membrane markers were analyzed by FACS: MHC-Class II, CD80, CD86 and CD40.

Figure 11:
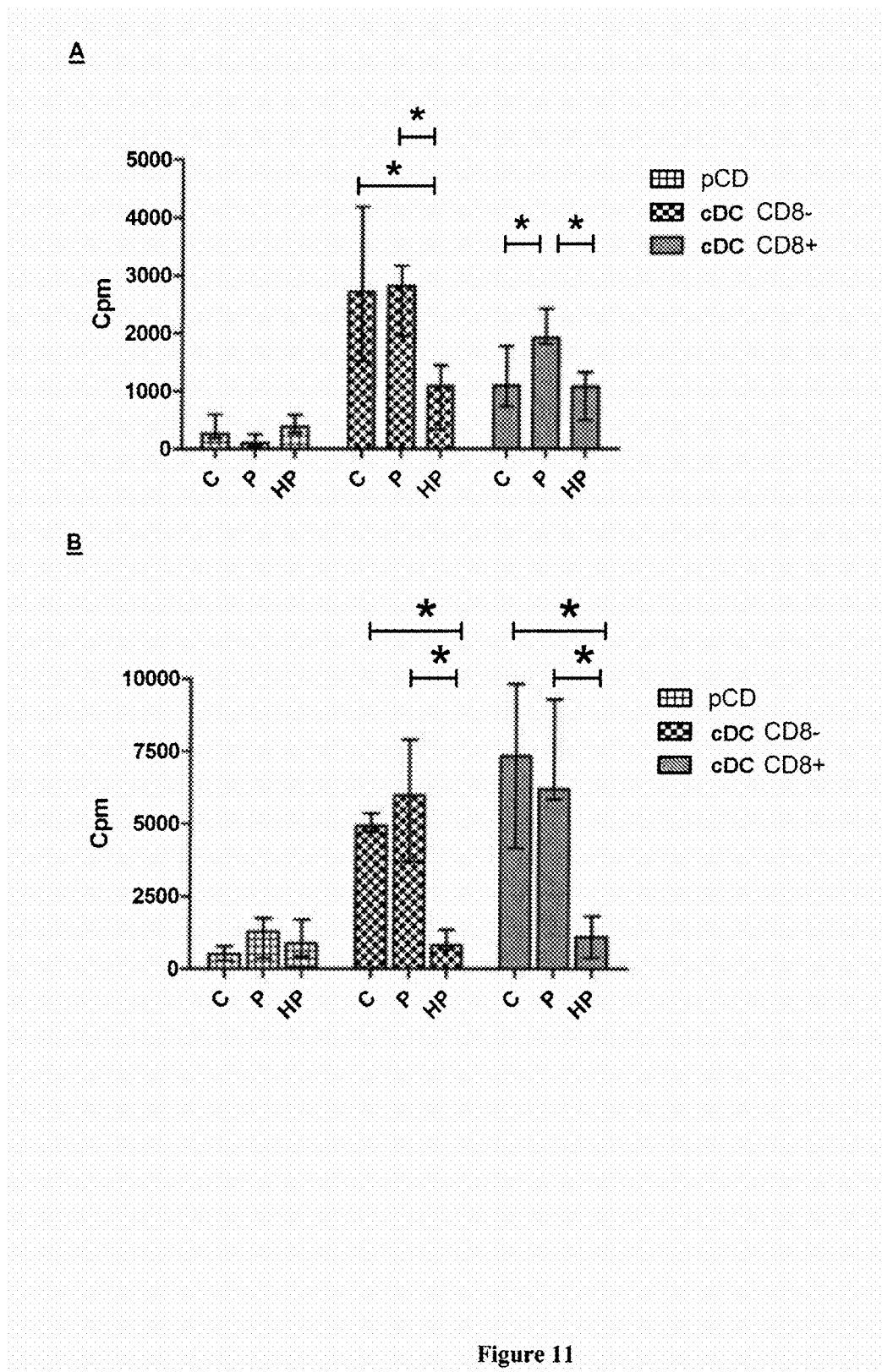

FIG. 11: Post-haemorrhagic SI reduces the capacity of cDCs to cause proliferation of T lymphocytes during MSSA pneumonia.

Each DC subset was sorted (A. non-stimulated DCs) and cultured ex vivo for 24 hours with CpG 1826 (5 µM): (B. stimulated DCs). Each subset was cultured with allogeneic CD4 and CD8 T lymphocytes for 3 days (DC/T ratio: 1/25). Lymphocyte proliferation was measured by cell incorporation of thymidine over a period of 8 hours. Each group comprised a pool of 5 animals. Data are expressed as the median±SEM and are representative of two independent experiments, each having the same statistical significance. pDC (square-ruled bars), CD8 cDC (chequered bars) and CD8$^+$ cDC (shaded bars). (*p≤0.05).

A. Proliferation of T lymphocytes in contact with non-stimulated DCs.

B. Proliferation of T lymphocytes in contact with DCs stimulated 24 hours with CpG.

Figure 12:
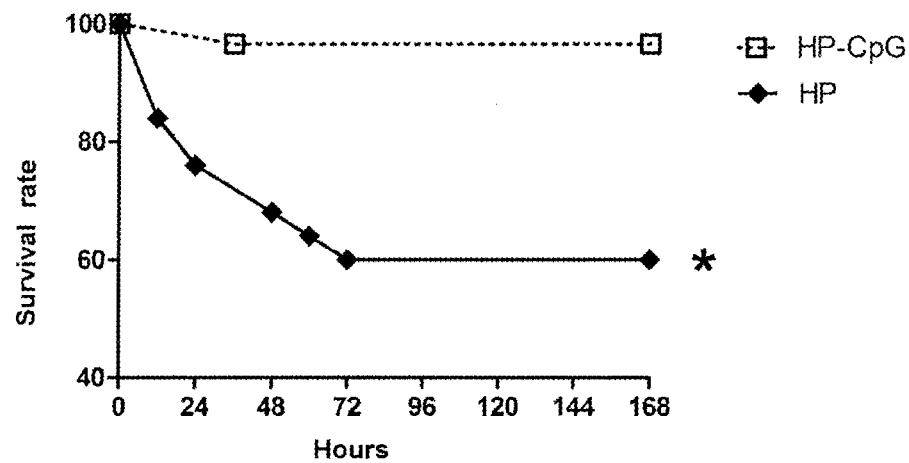

FIG. 12: After haemorrhagic shock, treatment with CpG-ODN prevents increased susceptibility of animals to MSSA pneumonia.

An intra-venous injection of CpG-ODN 1668 (100 µl to 100 µmol) (HP-CpG group) or the same volume of isotonic saline solution (HP group) was given immediately after resuscitation from haemorrhagic shock. Twenty-four hours later the mice were inoculated with 7×10$^6$ CFU of MSSA. The survival rate of each group was measured twice a day for 7 days (168 hours). Each group comprised 8 animals. Data are given as a percentage and are representative of three independent experiments each having the same statistical significance (*p≤0.05). HP Group (black diamonds), HP-CpG group (blank squares).

The present invention will be better understood in the light of the examples below based on the above-described figures.

These examples are given solely for illustration and in no way limit the subject of the present invention.

EXAMPLES

1. Material and Methods
1.1. Animals

Male Balb/cJ mice (20-24 grams) were obtained from the Janvier breeding company (Laval, France). Mice were kept on a day/night cycle of 12 hours with free access to food and drink. All handling operations were conducted in accordance with the principles laid down for the care of laboratory animals (NIH publication No 86-23, amended in 1985). Three groups were defined: Control (C group) consisting of cardiac puncture followed by sterile endo-tracheal instillation; Pneumonia (P group) having pneumonia alone; and Haemorrhage-Pneumonia (HP group) with multiple trauma (here haemorrhagic shock) given resuscitation followed by pneumonia.

1.2. Procedure for Obtaining Haemorrhagic Shock

A murine model of volume-controlled haemorrhagic shock followed by resuscitation, validated in the literature was used (Asehnoune et al. 2006 (A and B); Asehnoune et al. 2005; Robinson et al. 1991). The animals were anesthetized with 1.5 ml of Isoflurane® (Baxter, France). Trans-thoracic cardiac puncture using a 29 gauge needle was performed to sample within 45 seconds 30% of the blood volume (0.3 ml of blood/10 g body weight). The blood was sampled using a heparinized syringe (sodium heparinate, 5 U) and stored under agitation at 37° C. for 60 minutes. The blood volume was then restored by injection into the retro-orbital venous plexus.

1.3. Procedure for Obtaining *Staphylococcus aureus* Pneumonia

A strain of methicillin-sensitive *Staphyloccocus aureus* or <<MSSA>> (ATCC strain 29213) was cultured 16 hours at 37° C. in a tryptic soy medium (Grosseron, Saint Herblain, France). Immediately before use, the cultures were washed twice (centrifuged 10 minutes at 1000 g) and diluted in sterile isotonic saline solution for calibration by spectroscopy. The bacterial concentration was systematically controlled by quantitative culture.

The mice were anesthetized with Isoflurane® (Baxter, France) and placed in dorsal decubitus. An enteral nutrition needle (24-gauge) was used for catheterizing the trachea and injection of 70 µl of bacterial solution. Mice were then suspended 30 seconds by the incisors for better penetration of the inoculum. The intra-tracheal instillation level reached 100%.

1.4. Clinical Monitoring

Mortality was assessed twice a day for 7 days. The mice were weighed once a day for 5 days. Capillary glycaemia was measured using a haemaglucotest (Boehringer Ingelheim France), Venous blood gasometry, reflecting shock intensity and quality of resuscitation, was measured on central venous blood taken from the right atrium.

1.5. Measurement of Bacterial Spread of the Infection

After sacrifice, the lungs and spleen of the animals were mechanically homogenized under sterile conditions. The homogenates were subjected to a series of 1/10 dilutions and cultured at 37° C. on selective Chapman medium (Grosseron, Saint Herblain, France). After an incubation time of 48 hours, the bacterial colonies were counted and the results expressed as log 10 Colony Forming Units (CFU) per gram of organ. Staphylo slide reagent (Biorad, France) was used to differentiate between *S. aureus* and *S. non aureus*.

1.6. Histological Analysis

The lungs were taken and immediately placed in 4% formaldehyde. The fixed tissues were cut and stained with hematoxylin and eosin before microscope analysis.

1.7. Measurement of Myeloperoxidase Activity

As previously described in the literature (Kim et al. 2005), after sampling the lungs were weighed then mechanically homogenized at +4° C. for 25 seconds in 1 ml of buffer (50 mM potassium phosphate with 10 mM N-ethylmaleimide (pH=6). The protein homogenate was washed twice in the same iced buffer. Before sonication on ice (180 seconds), the protein residue was placed in suspension in 1 ml of potassium phosphate (50 mM, pH=6) containing 0.5% hexadecyl trimethylamonium. After 2-hour heat shock at +56° C., the myeloperoxidase activity of the supernatant was determined by measuring the oxidation of o-dianisidine by hydrogen peroxide (Kim et al. 2005).

1.8. Measurement of Pulmonary Endothelial Permeability

As previously described (Boutoille et al. 2009), albumin tagged with Fluorescein isothiocyanate (FITC-albumin, Sigma, Germany) was used to measure pulmonary endothelial permeability. Two hours after intra-peritoneal injection of 2 mg of FITC-albumin, the mice were euthanized by exsanguination, Lungs were than taken, mechanically homogenized in 1 ml of isotonic saline solution then centrifuged (4000 g for 10 minutes). The blood was centrifuged 10 minutes at 4000 g to collect the plasma. The quantity of FITC-albumin was measured by fluorimetry (excitation 487 nm and emission 520 nm) in the plasma and lung homogenate. The pulmonary endothelial permeability was then calculated using the following validated formula:

$$\text{Perm-}FITC\,(\%) = (((FL_{HS} - FL_N) \times W_H) - QFB)/((F_{BS} - F_{BN}) \times We \times 0.07 \times (1 - Hte))$$

where $FL_{HS}$ is the fluorescence of the pulmonary supernatant; $FL_N$ is the natural fluorescence of this supernatant measured without FITC-albumin; $F_{BS}$ is the fluorescence of the plasma; $We \times 0.07 \times (1 - Hte)$ is the plasma volume (We: weight of the mouse; Ht: haematocrit); $F_{BN}$ is the natural fluorescence of the plasma measured without administration of FITC-albumin; $W_H$ is the weight of the lungs; QFB, which is the proportion of fluorescence corresponding to residual intrapulmonary blood is calculated as follows:

$$(QFB = ((FL_{HS} - FL_N) \times Hb_{HS})/Hb)$$

where $Hb_{HS}$ is the residual haemoglobin level in the pulmonary supernatant and Hg is the haemoglobinaemia of the mouse before sacrifice.

1.9. Preparation of Lung Homogenates for Assay of Cytokines Using the ELISA Method The lungs were homogenized in iced buffer (1×PBS, pH 7.4, 0.1% Triton X-100) containing 1 mM of protease inhibitor (Sigma, France) (24). The supernatants obtained after centrifuging at +4° C. for 20 minutes at 12000 g were stored at −80° C. until analysis. The protein concentration of each sample was determined using the micro-BCA protein measurement kit with bovine serum albumin standardization (Pierce, England).

1.10. Cell Culture to Measure Blood Reactivity to LPS

A sample of 0.5 ml of blood was harvested when sacrificing the animals. The sample was 1/5 diluted in RPMI-1640 (Laboratoire de biotechnologies, Reims) with penicillin/streptomycin supplement. The diluted blood, 500 µL per well, was cultured with or without LPS LPS (*Escherichia coli* O111:B4 at 1 µg/ml) at 37.0° C. in an oven with 5% $CO_2$ (20). The supernatant of the cell cultures was centrifuged at 12000 g for 2 minutes and stored at −80° C. before ELISA assay. The concentrations of TNF-alpha, Interleukin (IL)-1β and macrophage-inflammatory protein-2 (MIP-2) were quantified by ELISA following the supplier's instructions (R&D Systems, France).

1.11. Isolation of Positive Splenic CD11c Cells

The spleens were digested with collagenase D (Roche Diagnostic, Germany) in RPMI 1640/1% foetal calf serum for 25 minutes at 37° C. 10 mM EDTA was added for the last 5 minutes before filtration (80 μm). The cells were washed in PBS before incubation for 15 minutes at +4° C. with an anti-CD11c anti-mouse antibody coupled to a metal bead. After washing, the cell suspension was enriched with CD11c+ cells by positive selection on a MACS separation column (Miltenyi, France). The purity of the CD11c+ cells routinely reached 85 to 95%.

1.12. Real-Time Reverse Transcription Polymerase Chain Reaction (Real Time RT-PCR)

The total RNA of the splenic CD11c+ cells was isolated with TRIzol (Invitrogen, France) and treated 45 minutes at 37° C. with 2 U of RQ1 DNAse (Promega, France). One microgram of RNA was subjected to reverse transcription with Superscript III reverse transcriptase (Invitrogen). One microliter of complementary DNA solution was subjected to real-time quantitative PCR in a BioRad iCycler iQ system using the QuantiTect SYBR Green PCR kit (Qiagen, France). Quantitative PCR consisted of 45 cycles of 30 seconds at 95° C. followed by 30 seconds at 60° C. The sequences of the primers for TNF-alpha, Interferon beta (IFNbeta), IL-10, IL-12 and glyceraldehyde-3-phosphate dehydrogenase (GAPDH) were selected using the "pick primer" software by NCBI (Table 1).

1.14. T lymphocytes/Dendritic Cells Co-Culture (Ouabed et al. 2008)

The DC subsets were sorted by FACS and maturated (stimulated DCs) or not maturated (non-stimulated DCs) 24 hours with CpG 1668 (Invivogen, France). The DCs were then cultured with allogeneic CD4+ and CD8+ T lymphocytes in a round-bottomed 96-well culture plate. After three days' culture at 37° C. with 5% $CO_2$, the cells were placed in contact for 8 hours with 0.5 μCi of [3H]TdR (GE Healthcare) per well. The cells were then harvested on a glass fibre filter to measure the incorporation of thymidine by scintillation (Packard Institute).

1.15. Statistical Analysis

GraphPad prism software (GraphPad Software, San Diego, Calif.) was used to perform statistical analysis. Survival rates were compared using a logrank test. Non-parametric continuous variables were expressed as the median±SEM or ±25-75$^{th}$ percentiles and compared using the Kruskall Wallis test followed by a Mann-Whitney test. $p \leq 0.05$ was the threshold of statistical significance.

2 Results 2.1. Pilot Study: Preparing a Murine Model of Post-Haemorrhagic Systemic Immunodepression (SI) Secondarily Exposed to *S. aureus* Pneumonia.

2.1.1 Effect of the Inoculum and of the Time Interval between Haemorrhagic Shock and MSSA Pneumonia on Mortality For the purpose of evidencing the effects of post-haemorrhagic SI on mortality, MSSA pneumonia was obtained with $7 \cdot 10^5$, $7 \cdot 10^6$ and $7 \cdot 10^7$ CFU of *S. aureus* 24 hours after causing haemorrhagic shock (HP group) and compared with the group in which only pneumonia was induced (P group).

TABLE 1

Sequences of primers for quantitative RT-PCR

| Primer | Forward primer (5'-3') | SEQ ID NO | Reverse primer (3'-5') | SEQ ID NO |
|---|---|---|---|---|
| TNF alpha | AAAGGGAGAGTGGTCAGGTTGC | 1 | GGCTGGCTCTGTGAGGAAGG | 2 |
| IFN beta | CCCTATGGAGATGACGGAGA | 3 | CTGTCTGCTGGTGGAGTTCA | 4 |
| IL-10 | TGGCATGAGGATCAGCAGGG | 5 | GGCAGTCCGCAGCTCTAGG | 6 |
| IL-12p40 | TGTGGAATGGCGTCTCTGTCTG | 7 | CAGTTCAATGGGCAGGGTCTCC | 8 |
| GAPDH | ACCACAGTCCATGCCATCAC | 9 | ACCTTGCCCACAGCCTTG | 10 |

The expression of GAPDH was used as reference to normalize the expression level of each gene. Quantitative gene expression was calculated with the 2-ΔΔCt method using splenic CD11c+ cells of Control mice as calibrator (Livak et al. 2001).

1.13. FACS Analysis

The total number of living spleen cells in suspension (PBS-Foetal Calf Serum-Azide) was counted on Malassez cell using the eosin exclusion test. The rat-derived anti-mouse antibodies used were obtained from the European cell culture collection. The antibody mixture used to exclude non-dendritic cells was obtained from BD Biosciences (United States): CD3-PE, CD19-PE, TCRb-PE, NK1.1-PE, Ter119-PE. The DC subsets were characterized by the following antibodies: SiglecH-APC Biosciences (United States), CD11c-PECy7, CD8-FITC, B220-PerCPCy5.5. DC maturation was assessed by the following biotinylated antibodies: anti-CD80, anti-CD86, anti-CD40 and anti-MHC Class II. The non-specificity of the antibodies was measured by adding Streptavidin-APC Cyanine 7 BD Biosciences (United States): A total of $4 \times 10^6$ cells for each antibody was counted.

Mortality was higher in the HP group compared with the P group for the weakest inocula (FIG. 1.A.B). The strongest inoculum led to 100% mortality in both groups (FIG. 1.C.). Since post-haemorrhagic SI is a dynamic process, the development of SI over time was evaluated. MSSA pneumonia was induced 2, 4, 8, 24, 48 or 96 hours after haemorrhagic shock (group HP-H2; -H4; -H8; H-24; H-48; H-96, respectively). Compared with pneumonia alone (P group), the survival rate in the HP group diminished significantly when the time between shock and pneumonia was increased from 4 to 24 hours, and a gradual recovery was observed over longer time periods (FIG. 1.D). An inoculum of *S. aureus* of $7 \cdot 10^6$ CFU (group P) and a time interval between haemorrhagic shock and pneumonia of 24 hours (group HP) were the optimal parameters for the study of SI. They were therefore used for the main study (FIG. 2). In the Control group (C), cardiac puncture without blood sampling or resuscitation was followed by an intra-tracheal instillation of sterile saline solution 24 hours later. The volume-controlled haemorrhage was obtained by cardiac puncture (0.3 ml/10 g) followed by reinjection of the removed blood 60 minutes later (Haemorrhage Pneumonia group, HP). Twenty-four hours after resuscitation, 70 µl of either $7\cdot10^6$ CFU of MSSA (pneumonia group P and HP group) or of sterile physiological solution (group C) were instilled in the trachea. Twenty-four hours (unless indicated otherwise) after the onset of the infection, the mice were euthanized and samples taken.

2.1.2 Haemorrhagic Shock Aggravates Weight Loss and the Biological Consequences of MSSA Pneumonia.

The clinical and biological consequences of post-haemorrhagic SI on the outcome of the infection were also measured. The mice in the HP group suffered the greatest weight loss (FIG. 3.A), more severe metabolic acidosis and a lower drop in glycaemia (FIG. 3.B) than the mice in the P group.

2.1.3. Post-Haemorrhagic SI Induces Bacteraemia During MSSA Pneumonia.

The local and systemic spread of the infection was evaluated 12, 24 and 48 hours after pneumonia with haemorrhagic shock (HP group) and without haemorrhagic shock (P group). No MSSA was evidenced in the lungs and spleen of control mice (C group). Lung bacterial clearance remained unchanged in the HP group compared with the P group (FIG. 4.A). On the other hand the systemic spread of the infection, evaluated by cultures of spleen homogenates, increased in intensity at the $24^{th}$ and $48^{th}$ hour in the HP group compared with the P group (FIG. 4.B). Bacteraemia was also more frequent after haemorrhagic shock at the $24^{th}$ and $48^{th}$ hour of the infection (FIG. 4.C).

2.1.4. Post-Haemorrhagic SI Aggravates Lung Lesions of MSSA Pneumonia.

Since lung bacterial clearance was not altered during post-haemorrhagic SI, the histo-pathological appearance of the lung over the course of the infection was evaluated. Healthy lung tissue is characterized by thin-walled aerated alveoli bordered by a single-cell layer of pneumocytes (FIG. 5.A). In the control mice (C group) the lung tissue appeared normal (FIG. 5.B). In the P group, on and after the $12^{th}$ and $24^{th}$ hours of infection, aggregates of immunity cells were observed as well as an onset of alveolar destruction with thickening of the walls (FIG. 5.C.E.). Histological recovery with aeration of the alveoli started on the $4^{th}$ day and was complete on the $7^{th}$ day (FIG. 5.G.I). In the HP group, at each time interval (FIG. 5.D.F.H.J), the aggregates of immune cells were more numerous and the alveolar lesions more severe than in the P group. Lung lesions had an earlier onset and recovery was longer in the HP group than in the P group.

The histological lesions of MSSA pneumonia were qualitatively more severe after haemorrhagic shock, with in particular an increase in the influx of immune cells (macrophages and polynuclear neutrophils). The accumulation in the lungs of polynuclear neutrophils was therefore evaluated quantitatively by assay of the myeloperoxidase activity of the lung tissue of the mice. At the $24^{th}$ hour of the infection, the accumulation of polynuclear neutrophils was higher in the HP group than in the P group (FIG. 6.A.). The polynuclear neutrophils produce radical species of oxygen in large quantity, which are the source of endothelial lesions (Rivkind et al. 1991). On account of the accumulation of these cells, pulmonary endothelial permeability (reflecting alveolar oedema) was measured. In the HP group, it showed a higher increase than in the P group (FIG. 6.B). In addition, lung concentrations of pro-inflammatory cytokines (TNF alpha, IL-1 beta and MIP-2) increased during the infection (FIG. 6.C.D.E) but the concentration of IL-1 beta was higher when pneumonia was preceded by haemorrhagic shock (FIG. 6.D).

2.1.5. Post-Haemorrhagic SI Increases Blood Hypo-Reactivity to LPS Following After MSSA Pneumonia.

As previously described by the Inventors (Asehnoune et al. 2006A) and other authors (Goebel et al. 2000; Spolarics et al. 2003), post-traumatic SI is characterized by a decrease in blood reactivity to the LPS of *E. coli* O111B4. Since the study on the secretion of cytokines on whole blood produces the same results as on isolated monocytes (Damsgaard et al. 2009), for technical reasons related to their murine model the Inventors chose to study hyporeactivity to LPS on whole blood. The production of TNF-alpha and of IL-1 beta was significantly diminished in the HP group compared with groups P and S (FIG. 7.A.B.) whereas the production of MIP-2 was also lower in groups HP and P compared with the C group (FIG. 7.C.).

2.2. Characterization of Innate Immunity Disorders Related to Post-haemorrhagic SI Following After MSSA Pneumonia.

At the time of the body's response to infection, the dendritic cells ensure the integration between innate and adaptive immunity and probably play a crucial role in regulating the immune dysfunction induced by haemorrhage. The reduction in the membrane expression of HLA-DR on circulating monocytes is at present the only marker of systemic immunodepression which has given corroborating results in terms of prediction of the onset of an infection, or syndrome of multi-visceral failure and of correlation with post-traumatic prognosis in general, without any causal link being shown. In the post-haemorrhagic SI model described herein, the infection is more serious when it is preceded by a haemorrhage. The number and the function of the dendritic cells were therefore compared as a function of the presence (HP group) or absence (P group) of haemorrhagic shock before the infection.

2.2.1. Number and Maturation of Splenic $CD11c^{high}$ Cells Following After MSSA Pneumonia Whether or Not Preceded by Haemorrhagic Shock.

The number of $CD11c^{high}$ cells, which represent the majority of DCs in the spleen, was reduced following after the infection whether preceded (HP group) or not preceded (P group) by haemorrhagic shock (FIG. 8.A.). The antigen-presenting capacities were measured by the membrane expression of the antigen-presenting molecules (MHC Class II), and co-stimulation molecules (CD80 and CD86). The membrane expressions of MHC Class II and of CD80 were reduced during MSSA pneumonia in both groups P and HP, whereas the membrane expression of CD86 was only reduced when haemorrhagic shock was induced before the onset of the infection (FIG. 8.B.). The membrane expression of CD40, the maturation marker of DCs, was not modified under the experimental conditions (FIG. 8.B.).

2.2.2. Post-Haemorrhaqic SI Reduces the Transcriptional Activity of $CD11c^+$ Cells Following After MSSA Pneumonia.

The $CD11c^+$ cells comprise all murine DCs. The mRNA levels of TNF-alpha, IFN beta and IL-12 were significantly high at the $6^{th}$ hour of infection in group P compared with group C (FIG. 9.A.B.C.) This increase was not observed if infection was preceded by haemorrhagic shock (group HP) (FIG. 9.A.B.C.). With regard to IL-10, the mRNA level dropped in the HP group compared with the C group whereas it remained unchanged for infection alone.

2.2.3. Post-Haemorrhagic SI Alters the Phenotypes of DC Subsets Over the Course of MSSA Pneumonia.

Three main DC subsets have been described to date (Merad et al. 2009): conventional DCs (cDCs) which comprise $CD8^+$ cDCs and $CD8^-$ cDCs; plasmacytoid DCs (pDCs). The number of $CD8^-$ cDCs was reduced 24 hours after pneumonia, whether preceded (HP group) or not preceded (P group) by an haemorrhagic shock, whereas the numbers of CD8+ cDCs and pDCs remained unchanged (FIG. 10.A). Regarding the pDCs, the haemorrhage induced before pneumonia (group HP) led to a significant reduction in antigen-presenting capacities (membrane expression of MHC-Class II, CD80 and CD86) compared with the inducing of pneumonia alone (P group) and the control group (C). The maturation of pDCs, reflected by the expression of CD40, was also reduced by the infection with haemorrhagic shock (HP group) or without haemorrhagic shock (group P), compared with the control group (C group) (FIG. 10.B.). With regard to the CD8+ cDCs, maturation and the antigen-presenting capacities were both reduced by the infection with haemorrhagic shock (HP group) or without haemorrhagic shock (P group) compared with the control group (C group, FIG. 10.C.). With regard to the CD8− cDCs, the antigen-presenting capacities were partly reduced (membrane expression of MHC-Class II and CD80) whereas maturation (membrane expression of CD40) remained unchanged in animals infected after (HP group) or without (P group) haemorrhagic shock compared with the control animals (C group, FIG. 10.D.).

2.2.4. Post-Haemorrhagic SI Reduces the Capacity of cDCs to Cause the Proliferation of T Lymphocytes During MSSA Pneumonia.

The collapse of the membrane markers studied by FACS during MSSA pneumonia (P group) was so high in the model described herein that the technical possibilities of evidencing a difference during post-haemorrhagic SI were limited. To fine-tune understanding of the functional disorders of DCs after haemorrhagic shock, the capacities of each DC subset to cause lymphocyte proliferation were studied without (FIG. 11.A.) and with (FIG. 11.B.) ex vivo CpG maturation of the DCs. The haemorrhagic shock (HP group) drastically reduced the capacities of the cDCs (CD8+ and CD8−) to cause proliferation of the T lymphocytes, with and without CpG maturation, compared with pneumonia alone (P group) (FIG. 11.A.B.). No difference could be observed in the pDC subset (FIG. 11.A.B.).

2.3. Effect of Preventive Treatment with CPpG-ODN or MPLA on Excess Mortality from MSSA Pneumonia in our Post-Haemorrhagic SI Model Since the three subsets of DCs were significantly altered by post-haemorrhagic SI, the Inventors tested the possibility of preventing excess mortality related to this disorder during MSSA pneumonia through treatment with a TLR-9 agonist, CpG-ODN, which triggers in vivo maturation of DCs under normal conditions (Askew et al. 2000) or using a TLR-4 agonist, MPLA, which triggers the maturation of conventional DCs in vivo (Mata-Haro et al. 2007). CpG 1668 (type B CpG-ODN, Invivogen, France), just like MPLA (Invivogen, France), significantly lowered mortality in the model that is described herein (FIG. 12 and data not shown). Inactive CpG-ODN (control), which is a TLR-9 agonist which does not activate its receptor, did not prevent infection-related mortality.

3 Additional Observations

The results presented in the foregoing confirm the critical role played by functional alterations of DCs in infections secondary to post-haemorrhagic SI. It is also shown that 1) Post-haemorrhagic SI increases mortality, systemic spread and the pulmonary lesions of *S. aureus* pneumonia; 2) the main subsets of DCs are altered by this disorder; 3) preventive treatment with CpG injected during the resuscitation phase after haemorrhagic shock allows the correction of excess mortality from *S. aureus* pneumonia related to post-haemorrhagic SI.

REFERENCES

Mathers et al. PloS Med. November 2006; 3(11):e442.
Patton et al. Lancet. September 2009; 374(9693):881-92,
Rincon-Ferrari et al. J Trauma. December 2004; 57(6):1234-40.
Papia et al. J Trauma. November 1999; 47(5):923-7.
SFAR, SRLF. The risk for and approaches to control nosocomial infections in ICUs: guidelines from SFAR/SRLF task force on nosocomial infections in ICUs reanimation. 2005; 14:463-71.
Keel et al. J Trauma. September 1996; 41(3):430-7; discussion 7-8.
Ditschkowski et al. Ann Surg. February 1999; 229(2):246-54.
Stephan et al. J Surg Res. June 1989; 46(6):553-6.
Wichmann et al. Crit Care Med. August 1998; 26(8):1372-8.
Asehnoune et al. Resuscitation. 2006A Jan; 68(1):127-33.
Asehnoune et al. Cytokine. 2006B May; 34(3-4):212-8.
Asehnoune et al. Ann Fr Anesth Reanim. March 2005; 24(3): 255-9.
Robinson et al. Crit Care Med. October 1991; 19(10):1285-93.
Kim et al. Am J Physiol Lung Cell Mol Physiol. May 2005; 288(5):L958-65.
Boutoille et al. Exp Lung Res. May 2009; 35(4):263-71.
Livak et al. Method. Methods. December 2001; 25(4):402-8.
Ouabed et al. J Immunol. 2008 May 1; 180(9):5862-70.
Rivkind et al. Circ Shock. January 1991; 33(1):48-62.
Goebel et al. Ann Surg. February 2000; 231(2):253-61.
Spolarics et al. Crit Care Med. June 2003; 31(6):1722-9.
Damsgaard et al. J Immunol Methods. 2009 Jan. 30; 340(2): 95-101.
Merad et al. Blood. 2009 Apr. 9; 113(15):3418-27.
Askew et al. J Immunol. 2000 Dec. 15; 165(12):6889-95.
Mata-Haro et al. (2007) Science 316: 1628-1632.
Leonard et al. (2007) Clin. Cancer Res. 13:6168-6174.
Venet et al. (2007) Crit. Care Med. 35:1910-1917.
Cheadle et al. (1991) Am. J. Surg. 161:639-645.
Baker et al. (1974) J Trauma. 14 :187-196.
Teasdale et al. (1974) Lancet 2: 81-84.
Osborn et al. Crit Care Med 2004; 32(11):2234-40.

The invention claimed is:

1. A method for the prophylactic treatment of septic complications of post-traumatic systemic immunodepression in a patient in need thereof, comprising administering a pharmaceutical composition comprising at least one agonist of at least one Toll Like receptor (TLR) chosen from TLR 4 and 9, to a hospitalized patient suffering from one or more traumatic injuries wherein said TLR 4 agonist is monophosphoryl lipid A (MPLA) or deacylated 3-O-monophosphoryl lipid A (3D-MPLA).

2. A method according to claim 1, wherein said TLR 9 agonist is a CpG oligodeoxynucleotide (CpG ODN).

3. A method according to claim 2, wherein said CpG ODN is a synthetic oligodeoxynucleotide of at least 8 nucleotides containing at least one non-methylated CpG dinucleotide.

4. A method according to claim 2, wherein said CpG ODN contains no more than 100 nucleotides.

5. A method according to claim 4, wherein said CpG ODN contains 8 to 40 nucleotides.

6. A method according to claim 1, wherein said immunodepression is characterized by:
   a) a decrease in the ex vivo production level of pro-inflammatory cytokines induced by white blood cells after stimulation by LPS of gram negative bacilli, compared with the production level observed in a healthy individual; and/or
   b) a decrease in the expression level of HLA-DR on the antigen-presenting cells of said patient, compared with the expression level observed in a healthy individual.

7. A method according to claim 6, wherein the HLA-DR expression level on monocytes of said patient over the 24 hours following the traumatic injury or injuries is reduced compared with the expression level observed in a healthy individual.

8. A method according to claim 1, wherein said septic complications are nosocomial infections.

9. A method according to claim 8, wherein said nosocomial infections are bacterial.

10. A method according to claim 1, wherein said traumatized patient has at least two traumatic injuries among which is at least one life-threatening injury.

11. A method according to claim 10, wherein said traumatized patient has an injury severity score (ISS) of at least 16 and/or a severe brain injury defined by a Glasgow score (CGS) of less than 8.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: artificial
<220> FEATURE:

<223> OTHER INFORMATION: Forward primer TNF alpha

<400> SEQUENCE: 1
aaagggagag tggtcaggtt gc                                    22

<210> SEQ ID NO 2
<211> LENGTH: 20
<212> TYPE: DNA
<213> ORGANISM: artificial
<220> FEATURE:
<223> OTHER INFORMATION: Reverse primer TNF alpha

<400> SEQUENCE: 2
ggctggctct gtgaggaagg                                       20

<210> SEQ ID NO 3
<211> LENGTH: 20
<212> TYPE: DNA
<213> ORGANISM: artificial
<220> FEATURE:
<223> OTHER INFORMATION: Forward PRIMER IFN beta

<400> SEQUENCE: 3
ccctatggag atgacggaga                                       20

<210> SEQ ID NO 4
<211> LENGTH: 20
<212> TYPE: DNA
<213> ORGANISM: artificial
<220> FEATURE:
<223> OTHER INFORMATION: Reverse primer IFN beta

<400> SEQUENCE: 4
ctgtctgctg gtggagttca                                       20

<210> SEQ ID NO 5
<211> LENGTH: 20
<212> TYPE: DNA
<213> ORGANISM: artificial
<220> FEATURE:
<223> OTHER INFORMATION: Forward primer IL-10

<400> SEQUENCE: 5
tggcatgagg atcagcaggg                                       20

<210> SEQ ID NO 6
<211> LENGTH: 19
<212> TYPE: DNA
<213> ORGANISM: artificial
<220> FEATURE:
<223> OTHER INFORMATION: Reverse primer IL-10

<400> SEQUENCE: 6
ggcagtccgc agctctagg                                        19

<210> SEQ ID NO 7
<211> LENGTH: 22
<212> TYPE: DNA
<213> ORGANISM: artificial
<220> FEATURE:
<223> OTHER INFORMATION: Forward primer IL-12p40

<400> SEQUENCE: 7
tgtggaatgg cgtctctgtc tg                                    22

<210> SEQ ID NO 8

-continued

```
<211> LENGTH: 22
<212> TYPE: DNA
<213> ORGANISM: artificial
<220> FEATURE:
<223> OTHER INFORMATION: Reverse primer IL-12p40

<400> SEQUENCE: 8
cagttcaatg ggcagggtct cc                                              22

<210> SEQ ID NO 9
<211> LENGTH: 20
<212> TYPE: DNA
<213> ORGANISM: artificial
<220> FEATURE:
<223> OTHER INFORMATION: Forward primer GAPDH

<400> SEQUENCE: 9
accacagtcc atgccatcac                                                 20

<210> SEQ ID NO 10
<211> LENGTH: 18
<212> TYPE: DNA
<213> ORGANISM: artificial
<220> FEATURE:
<223> OTHER INFORMATION: Reverse primer GAPDH

<400> SEQUENCE: 10
accttgccca cagccttg                                                   18
```